United States Patent [19]

Ukkonen et al.

[11] 4,279,827
[45] Jul. 21, 1981

[54] PROCESS FOR THE PREPARATION OF A β-SITOSTEROL CONCENTRATE CONTAINING LESS THAN 5% BY WEIGHT OF α-SITOSTEROL

[75] Inventors: Keijo A. Ukkonen; Esa J. Simpura, both of Lappeenranta, Finland

[73] Assignee: Oy Kaukas AB, Lappeenranta, Finland

[21] Appl. No.: 87,517

[22] Filed: Oct. 23, 1979

[30] Foreign Application Priority Data

Oct. 27, 1978 [FI] Finland .................................. 783279

[51] Int. Cl.³ .............................................. C07J 9/00
[52] U.S. Cl. .............................................. 260/397.25
[58] Field of Search .................................. 260/397.25

[56] References Cited

U.S. PATENT DOCUMENTS

| | | | |
|---|---|---|---|
| 3,983,147 | 9/1976 | Senda et al. | 260/397.25 |
| 4,044,031 | 8/1977 | Johansson et al. | 260/397.25 |
| 4,091,035 | 5/1978 | Clark | 260/397.25 |

Primary Examiner—Elbert L. Roberts
Attorney, Agent, or Firm—Young & Thompson

[57] ABSTRACT

Process for the preparation of a β-sitosterol concentrate containing less than 5% by weight of a α-sitosterol from sitosterol concentrates derived from plants by treating the sitosterol concentrate with a solvent mixture containing aromatic and/or aliphatic hydrocarbons as well as esters and, in addition, possible small amounts of other solvents.

4 Claims, 1 Drawing Figure

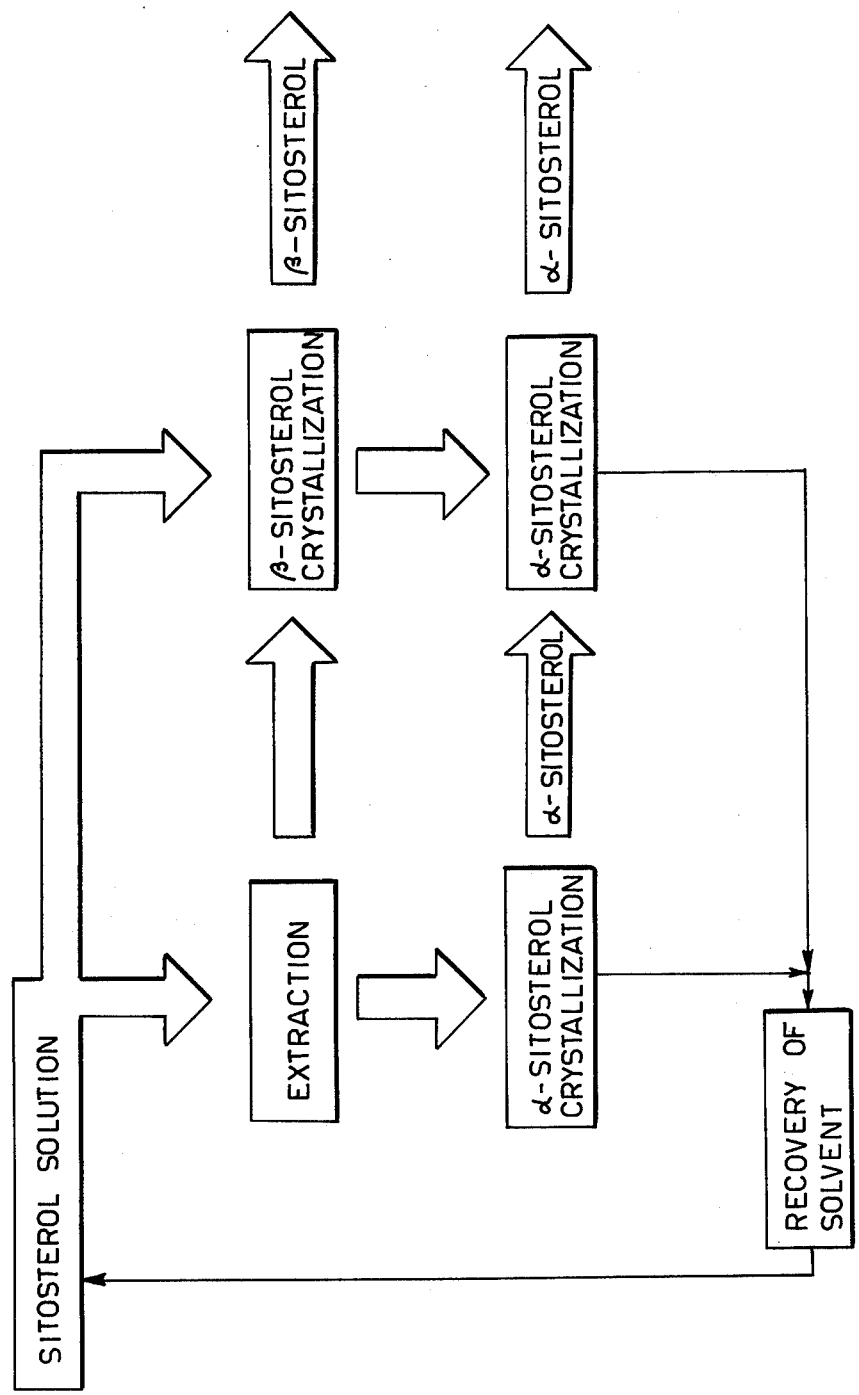

PROCESS FOR THE PREPARATION OF A β-SITOSTEROL CONCENTRATE CONTAINING LESS THAN 5% BY WEIGHT OF α-SITOSTEROL

This invention relates to a process for the preparation of a β-sitosterol concentrate containing less than 5% by weight of α-sitosterol from sitosterol concentrates derived from plants, such as hardwood, by treating the sitosterol concentrate with a solvent mixture containing aromatic and/or aliphatic hydrocarbons as well as esters and, in addition, possibly small amounts of ketones, alcohols, organic and inorganic acids and water.

The main part of the unsaponifiable substance in extractants of hardwood consists of sterols: campesterol, β-sitosterol and α-sitosterol (vide Jensen, W., Puukemina (Wood Chemistry), 2nd edition, SPIY, Helsinki, 1977, pp. 205-212). The sterols are present in the wood extractant either as free alcohols or in esterified form together with the fatty acids contained by the extractant. Hardly any α-sitosterol is present in the extractants of softwood.

In sulphate process used in the production of cellulose, the extractant in the wood is separated as soap on the surface of the so-called black liquor. The crude soap contains the fatty and resin acids of the extractant as sodium salts and the so-called unsaponifiable fraction (i.e. the neutral substance) as free alcohols and hydrocarbons. A process has been developed by means of which this neutral substance in soap can be isolated from the crude soap (U.S. Pat. No. 3,965,085 and Finnish Pat. No. 50,884). The unsaponifiable fraction so separated from the soap contains about 20-25% of sterols. Of this quantity, β-sitosterol amounts to more than one half. If the soap has included considerable amounts of hardwood, for example, birch, the α-sitosterol content of the unsaponifiable fraction is also quite high, even 6-10% of the total quantity of unsaponifiables.

A process is known by means of which a sitosterol concentrate can be prepared from said neutral substance of crude soap (U.S. Pat. No. 4,044,031 and Finnish Application No. 772,064). According to said known process, the starting material comprises extractants of wood and plants, namely the neutral substance in crude soap, and the separation is based on a liquid/liquid extraction from a non-polar phase into a polar phase. The product obtained is a so-called sitosterol concentrate the α-sitosterol content whereof may amount even to one third of the total quantity of the sitosterol concentrate.

According to the process of the invention, the starting material is a sitosterol concentrate prepared from extractants of wood and plants by means of known processes for the separation of sitosterol (for example, by means of the process according to the above-mentioned U.S. Pat. No. 4,044,031); the separation is primarily based on crystallization from a precisely defined, polar solvent mixture, and also on extraction from a polar phase into a less polar phase. The product obtained comprises a β-sitosterol nearly free of $\alpha_2$-sitosterol of a so-called technical quality, and α-sitosterol.

A process has also been developed for the separation of α-sitosterol from β-sitosterol (U.S. Pat. No. 2,866,797). According to this process, α-sitosterol is separated by using a mixture of hydrocarbons and chlorinated hydrocarbons. However, chlorinated hydrocarbons are rather difficult compounds to use in processes, for example, because they are undesirable compounds as far as industrial hygiene is concerned. In addition, said process was actually developed for the preparation of sitosterol concentrates but not for the removal of $\alpha_2$-sitosterol. Thus, by means of said known process, a pure product is obtained only in case that the starting material contains no $\alpha_2$-sitosterol.

According to a preferred process of the invention, β-sitosterol is separated from a sitosterol concentrate by crystallizing it from the solvent mixture having the following composition:

30-90 parts by weight, preferably 70 parts by weight of hexane 5-20 parts by weight, preferably 10 parts by weight of xylene 2-10 parts by weight, preferably 9 parts by weight of ethyl acetate 0-2 parts by weight, preferably 1 part by weight of water 0-2 parts by weight, preferably 1 part by weight of acetic acid 0-2 parts by weight, preferably 1 part by weight of methanol 0-5 parts by weight, preferably 5 parts by weight of acetone.

According to a second preferred process, β-sitosterol is separated with a solvent mixture having the following composition:

20-50 parts by weight, preferably 35 parts by weight of hexane 5-30 parts by weight, preferably 10 parts by weight of xylene 2-10 parts by weight, preferably 9 parts by weight of ethyl acetate 0-2 parts by weight, preferably 1 part by weight of water 0-2 parts by weight, preferably 1 part by weight of acetic acid 0-2 parts by weight, preferably 1 part by weight of methanol 5-10 parts by weight, preferably 25 parts by weight of acetone 1-35 parts by weight, preferably 20 parts by weight of hydrochloric acid.

Thus, by means of the process according to the invention, a technical β-sitosterol free of $\alpha_2$-sitosterol is obtained from sitosterol concentrates. The essential feature in the process is the removal of $\alpha_2$-sitosterol. By means of the new process, the α-sitosterol concentration of a β-sitosterol concentrate can be reduced to less than 3% by weight. By means of several crystallizations very low α-sitosterol concentrations are obtained. The α-sitosterol can be separated in crystalline form by means of concentrating the mother liquor.

Thus, by means of the process according to the invention both β-sitosterol and α-sitosterol are recovered. The main principle of the invention appears from FIG. 1.

In the pharamceutical industry, β-sitosterol can be used as starting material in the preparation of steroids. The production of steroid intermediates is normally carried out mircrobiologically by utilizing fermentation processes. In these processes, α-sitosterol is a useless or even an undesirable component.

If steroid intermediate is prepared synthetically, α-sitosterol is unnecessary in the raw material. In some syntheses, α-sitosterol may be an undesirable compound.

α-sitosterol as such can be used as an antioxidant (Sims. R. J., Fioriti, J. A. and Kanuk, M. J. JAOCS, 49 (1972) 298) and even as a preserving agent in the food industry. Also emulgators can be prepared from α-sitosterol, and it can also be used as a blood cholesterol reducing agent, for example, in dietic food (Less, A. M., Mok, H. Y. I., Less, R. S., McCluskey, M. A. and Grundy, S. M., Atherosclerosis 28 (1977) 325).

The production of β-sitosterol suitable for use in the pharmaceutical industry requires the reduction of the proportion of α-sitosterol in the sitosterol concentrate to less than 5% by weight. As mentioned earlier, the α-sitosterol concentrate obtained can again be used as such for other purposes.

The following examples will further illustrate the invention.

EXAMPLE 1

10 g of a sterol concentrate containing about 20–25% of α-sitosterol was dissolved in a solvent containing 110 ml of hexane, 10 ml of ethyl acetate, 20 ml of p-xylene and 1 ml of water. The dissolution took place by refluxing the mixture. The crystallization took place at +5° C. within about 1 hour. The yield of β-sitosterol was 40%, and the purity in relation to α-sitosterol was 2.5%.

The mother liquor was evaporated to half its volume to crystallize an α-sitosterol concentrate. The yield was about 30%, and the concentrate contained about 60% of α-sitosterol.

EXAMPLE 2

The same procedure was used as in Example 1 but using the following solvent mixture: 110 ml of hexane, 20 ml of ethyl acetate, 10 ml of p-xylene and 1 ml of water. The yield of β-sitosterol was 50%, and the purity in relation to α-sitosterol was 2%.

EXAMPLE 3

The same procedure was used as in Example 1 but using the following solvent mixture: 110 ml of hexane, 20 ml of methyl acetate and 20 ml of p-xylene. The yield of β-sitosterol was 50%, and the purity in relation to α-sitosterol was 2.5%.

EXAMPLE 4

The same procedure as used as in Example 1, but instead of ethyl acetate butyl acetate was used. The yield was 55%, and the α-sitosterol content was 2.2%.

EXAMPLE 5

The same procedure was used as in Example 1, but instead of p-xylene benzene was used. The yield was 55%, and the α-sitosterol content was 2.3%.

EXAMPLE 6

The same procedure was used as in Example 1, but as crystallization solution 100 ml of hexane and 40 ml of ethyl acetate were used. The yield was 50%, and the α-sitosterol content was 3%.

EXAMPLE 7

The same procedure was used as in Example 6, but instead of ethyl acetate butyl acetate was used. The yield was 50%, and the sitosterol content was 3%.

EXAMPLE 8

A sitosterol concentrate which was prepared according to the U.S. Pat. No. 4,044,031 and whereof 2% by weight was included in a solution containing 70% by weight of methanol, 15% by weight of acetone, 10% by weight of hexane and 5% by weight of water was extracted with hexane and ethyl acetate (80% by weight of hexane and 20% by weight of ethyl acetate). The extraction yield was 70% and the crystallization yield from the extraction solution 70%, the total yield thus being about 50%, and the α-sitosterol concentration 2.5%.

EXAMPLE 9

The same procedure was used as in Example 8, but instead of ethyl acetate butyl acetate was used. The total yield was 50%, and the α-sitosterol concentration was 3%.

EXAMPLE 10

The same procedure was used as in Example 1, but instead of water acetic acid was used. The yield was 50%, and the α-sitosterol concentration was about 3%.

EXAMPLE 11

The same procedure as used as in Example 1, but instead of water methanol was used. The yield was 50%, and the α-sitosterol concentration was 3%.

EXAMPLE 12

The same procedure was used as in Example 1, but instead of water a mixture of water and acetone (1:1 parts by weight) was used. The yield was 50%, and the α-sitosterol concentration was 3%.

EXAMPLE 13

The same procedure was used as in Example 1, but one half of the ethyl acetate was substituted by acetone. The yield was 50%, and the α-sitosterol concentration was 2.5%.

EXAMPLE 14

The same procedure was used as in Example 1, but one half of the hexane was substituted by a mixture of acetone and hydrochloric acid (35% by weight) (1:1 parts by weight). The crystallization yield was 64%, and the $\alpha_2$-sitosterol concentration was 0.9%.

EXAMPLE 15

The same procedure was used as in Example 1, but hydrochloric acid was added in an amount amounting to one half of the amount of ethyl acetate (35% by weight). The crystallication yield was 58%, and the $\alpha_2$-sitosterol concentration was 0.5%.

What we claim is:

1. A process for the removal of α-sitosterol from sitosterol concentrates based on plants to obtain a β-sitosterol concentrate containing less than 5% by weight of α-sitosterol, comprising dissolving a sitosterol concentrate containing β-sitosterol and more than 5% by weight of a α-sitosterol, in a solvent mixture consisting essentially of 30–90 parts by weight of hexane
5–30 parts by weight of xylene
2–10 parts by weight of ethyl acetate
0–2 parts by weight of water
0–2 parts by weight of acetic acid
0–2 parts by weight of methanol
0–5 parts by weight of acetone, and
cooling the resultant solution to about 5° C. thereby to separate by crystallization from said resultant solution $\beta$-sitosterol containing less than 5% by weight of $\alpha$-sitosterol.

2. A process as claimed in claim 1, wherein the composition of the solvent mixture is as follows:
about 70 parts by weight of hexane
about 10 parts by weight of xylene
about 9 parts by weight of ethyl acetate
about 1.0 parts by weight of water
about 1.0 parts by weight of acetic acid
about 1.0 parts by weight of methanol
about 5.0 parts by weight of acetone.

3. A process for the removal of $\alpha$-sitosterol from sitosterol concentrates based on plants to obtain a $\beta$-sitosterol concentrate containing less than 5% by weight of $\alpha$-sitosterol, comprising dissolving a sitosterol concentrate containing $\beta$-sitosterol and more than 5% by weight of a $\alpha$-sitosterol, in a solvent mixture consisting essentially of
20–50 parts by weight of hexane
5–30 parts by weight of xylene
2–10 parts by weight of ethyl acetate
0–2 parts by weight of water
0–2 parts by weight of acetic acid
0–2 parts by weight of methanol
5–10 parts by weight of acetone
1–35 parts by weight of hydrochloric acid,
and cooling the resultant solution to about 5° C. thereby to separate by crystallization from said resultant solution $\beta$-sitosterol containing less than 5% by weight of a $\alpha$-sitosterol.

4. A process as claimed in claim 3, wherein the composition of the solvent mixture is as follows:
about 35 parts by weight of hexane
about 10 parts by weight of xylene
about 9 parts by weight of ethyl acetate
about 1.0 parts by weight of water
about 1.0 parts by weight of acetic acid
about 1.0 parts by weight of methanol
about 25 parts by weight of acetone
about 20 parts by weight of hydrochloric acid.

* * * * *